United States Patent [19]
Johnston

[11] 4,164,539
[45] Aug. 14, 1979

[54] CATALYTIC GAS DETECTOR

[75] Inventor: James S. Johnston, Bognor Regis, England

[73] Assignee: Rosemount Engineering Company Limited, Great Britain

[21] Appl. No.: 828,662

[22] Filed: Aug. 29, 1977

[30] Foreign Application Priority Data

Aug. 31, 1976 [GB] United Kingdom ............... 36068/76

[51] Int. Cl.² ............................................. G01N 27/16
[52] U.S. Cl. .................................... 422/96; 23/232 E; 340/633; 422/97
[58] Field of Search ............. 23/232 E, 254 E, 255 E; 340/237 R, 237 S, 633; 338/34; 324/71 R, 71 SN; 422/94–98

[56] References Cited

U.S. PATENT DOCUMENTS

| | | | |
|---|---|---|---|
| 3,201,736 | 8/1965 | Ovshinsky | 324/71 SN UX |
| 3,271,591 | 9/1966 | Ovshinsky | 324/71 SN UX |
| 3,578,409 | 5/1971 | Silverman et al. | 23/232 E X |
| 3,581,555 | 6/1971 | Cline | 23/232 E X |
| 3,595,621 | 7/1971 | Andreatch | 23/232 E X |
| 3,695,848 | 10/1972 | Taguchi | 324/71 SN X |
| 3,714,562 | 1/1973 | McNerney | 338/34 X |
| 3,960,495 | 6/1976 | Tantram | 23/232 E |

*Primary Examiner*—Michael S. Marcus
*Attorney, Agent, or Firm*—Nickolas E. Westman

[57] ABSTRACT

A catalytic gas detector is formed as a sandwich and comprises two flat printed film resistance thermometer sensors back-to-back with a layer of thermally insulating material between them. A coating of a suitable catalytic substance covers an exposed flat face of one of the two sensors.

9 Claims, 4 Drawing Figures

CATALYTIC GAS DETECTOR

BACKGROUND OF THE INVENTION

The present invention relates to catalytic gas detectors.

It is well known to use a pair of resistance thermometer sensors, one of which is coated with a suitable catalyst, for detecting the presence of a combustible or decomposible gas or gas mixture. Typically, current is passed through the thermometer sensors to heat them to a temperature at which the combustion or decomposition reaction of the gas or gas mixture to be detected can be catalysed by the catalytic coating. A typical temperature is 400° C. If, for example, a combustible gas mixture is present, combustion occurs at the catalytic coating, raising the temperature of the coated sensor above that of the uncoated. This temperature difference is sensed by using a suitable electric circuit and can indicate the presence and concentration of the gas.

The composition of the catalytic coating is a matter of choice depending on the reaction which it is desired to catalyse. Numerous catalytic substances are known for both combustion and decomposition reactions. Thus, the term "catalytic coating" used hereinafter should be considered to include a coating of any catalytic substance useful in catalysing a gaseous combustion and/or decomposition reaction.

SUMMARY OF THE INVENTION

According to the present invention a catalytic gas detector is formed as a sandwich comprising two resistant thermometer sensor bodies and a thermally insulating member between the two bodies such that the surface area of the sandwich is less than the combined surface area of the two sensor bodies, each sensor body comprising a substrate of electrically insulating material and mounted thereon in thermal contact therewith a conducting path of material having a temperature dependant coefficient of resistance, the thermally insulating member having a lower thermal conductivity than the material of the substrates, and one of the sensor bodies having a catalytic coating on an exposed surface portion thereof.

The present invention has the advantage of reducing heat loss from the gas detector when it is heated to a temperature above that of the surrounding gas. Thus, the electrical power required to heat the detector is similarly reduced. It will be appreciated that when two separate resistance thermometer sensor bodies, one having the catalytic coating, are suspended in a gaseous medium, heat loss from the bodies when they are at a particular temperature above the gas is approximately proportional to the total surface area of the bodies. By combining the two bodies in a sandwich with a reduced total surface area, the rate of heat loss is reduced. Thus, to maintain the two sensor bodies at the desired temperature, less electrical power is required. The thermally insulating member in the middle of the sandwich will permit a temperature differential to arise between the two bodies when a combustion or decomposition reaction occurs at the catalytic coating on the exposed surface portion of one of the bodies. It will be understood that, since there is thermal contact between the conducting path and the substrate of each sensor body, each sensor body as a whole tends to be at a substantially uniform temperature. The thermally insulating member is made of a material having a thermal conductivity which is lower than that of the material of the substrates so that the temperature differential between the sensor bodies can be established.

Any conduction of heat through the thermally insulating member from one sensor body to the other will result in a reduction in the sensitivity of the detector. However, it is considered that this loss of sensitivity does not seriously detract from the overall advantages of the invention.

Preferably, the sensor bodies are formed as substantially equally sized flat plates and are disposed in parallel planes with the thermally insulating member sandwiched between them. Then conveniently, for each sensor body, the substrate is a substantially flat plate and the conducting path comprises a conductive vitreous film deposited on a back surface of the substrate. The sensor bodies may then be disposed back to back in said parallel planes, with said back surfaces facing inwards against the thermally insulating member, and the catalytic coating may cover the entire front surface of one of the sensor bodies.

Special and particular advantages arise from the above application of the present invention, using flat, typically printed, film resistance thermometer sensors. With such printed film sensors, the conducting path is usually printed on one face of the substrate. The limitations of printing techniques make it very difficult to print very fine conducting paths of sufficient length on small substrate chips. Thus, for similar ice point resistances, a printed film resistance thermometer sensor may have a somewhat larger surface area than the typically used hand wound resistance thermometer sensors. Nevertheless, it is most desirable to employ printed film sensors since such devices can be produced and accurately trimmed to have highly standardised and reproducible characteristics. By employing the present invention, the total surface area of a catalytic gas detector including two printed film resistance thermometer sensors can be reduced, thereby counteracting any inherent disadvantage resulting from the size of the printed film sensors, and enabling the inherent advantage of such film sensors to be utilised.

Furthermore, it will be appreciated that the typical shape of printed film resistance thermometer sensors, i.e. a flat, thin, rectangular plate or chip, especially lends itself to the formation of the sandwich of the present invention. The thermally insulating member preferably comprises a substantially flat sheet of substantially the same size as the two flat sensor bodies.

The present invention further envisages a catalytic gas detector formed as a sandwich as described above in combination with an electrical circuit arranged for supplying current to the conducting paths of the two sensor bodies to heat the bodies to a predetermined temperature above ambient and responsive to relative changes in the temperatures of the two sensor bodies resulting from combustion or decomposition of a gas at the catalytic coating to provide an indication of the presence of said gas. Preferably, the electrical circuit is a bridge circuit and there is a meter connected between balance points of the bridge for indicating the presence of said gas.

DESCRIPTION OF THE PREFERRED EMBODIMENTS

Figure 1:
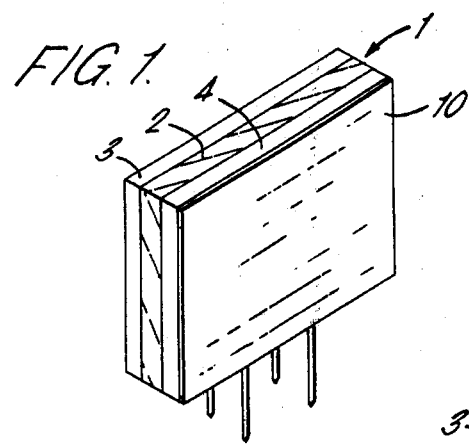
FIG. 1 illustrates a sandwich detector formed of a pair of printed film resistance thermometer sensors.
Figure 2:
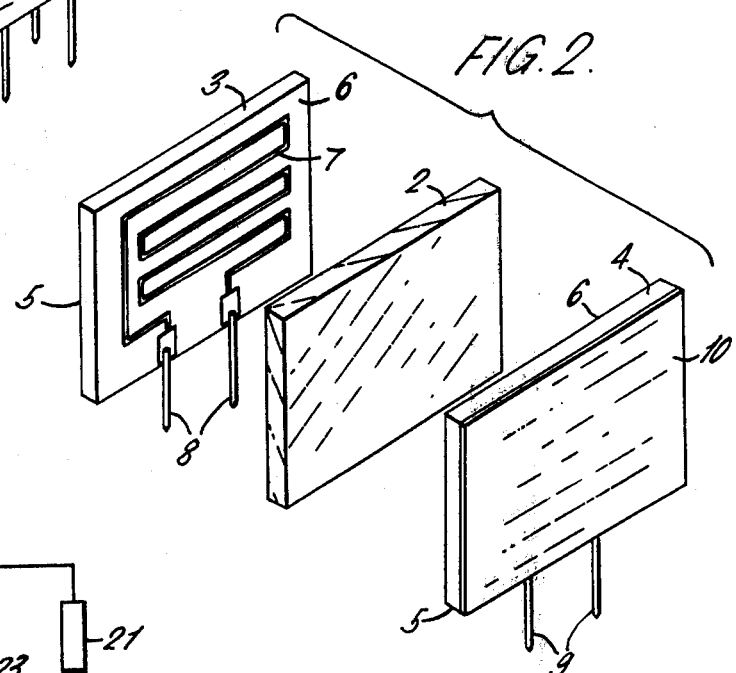
FIG. 2 is an exploded view illustrating the main parts of the detector of FIG. 1.

Referring to FIGS. 1 and 2, a catalytic gas detector is formed as a sandwich 1 comprising a thermally insulating sheet 2 sandwiched between printed film resistance thermometer sensors 3 and 4. Each printed film resistance thermometer sensor is formed as a body comprising a flat rectangular substrate 5 of electrically insulating material. On the inwardly facing or back surface 6 of each substrate 5 there is printed an electrically conductive path 7 of a material having a temperature dependent coefficient of resistance. The path 7 is typically formed, as shown in FIG. 2, as a series of meanders or zig zags, with the ends of the path adjacent an edge of the substrate formed as enlarged pads. Pins 8 and 9 are provided fixed in electrical contact with these pads, for example by compression welding, for connecting the paths 7 in an external electric circuit. A catalytic coating 10 is provided on the outwardly facing or front surface of one of the two substrates 5. The composition of the catalytic coating 10 is chosen to catalyse a gaseous combustion or decomposition reaction of the gas or gas mixture to be detected.

Each of the sensor bodies 3 and 4 may be formed by printing the pattern of the conductive path 7 on the back surface 6 using an ink comprising a platinum rich frit in a solvent. The printed substrate is then heated to dry off the solvent and fired to vitrify the frit as a hard conductive film firmly bonded to the surface of the substrate. The substrates 5 may be formed of any of the known insulating and dielectric materials, provided that they are capable of withstanding both the heat of firing when vitrifying the film and the temperatures of operation of the complete detector. Many known ceramic refractory substances are suitable including alumina.

The thermally insulating member 2 is, as shown in FIG. 2 formed as a rectangular sheet of substantially the same size as the sensor bodies 3 and 4. The member 2 is made of a material having a lower thermal conductivity than that of the substrates 5, so that a temperature differential can be produced between the two sensor bodies. Thus, the member 2 may comprise a refractory fibre mat formed of fibres of, for example, alumina, zirconia or glass. Furthermore, it is essential for obtaining the advantages of the present invention that the member 2 is sufficiently thin so that the total exposed area of its edges is less than the area of the two back faces 6 of the sensor bodies 3 and 4. The pins 8 and 9 may be formed of platinum to facilitate bonding with the platinum rich vitreous film of the paths 7, or they may be formed of gold.

In one example of a detector sandwich as illustrated in FIGS. 1 and 2, each resistance thermometer sensor body comprises a thin alumina plate, with printed thereon a conductive path having an ice point resistance of 10Ω. The sensor body so formed is 3 mm square and 0.25 mm thick. The insulating member 2 comprises a matt of zirconia fibres, also 3 mm square and approximately 0.25 mm thick. The three elements of the sandwich are bonded together as shown in FIG. 1, for example by an electrically insulating cement. The total surface area of the assembled detector sandwich is 27 sq. mm, whereas the surface area of the two resistance thermometer sensor bodies 3 and 4 is 42 sq. mm. Thus there is a reduction of surface area of approximately 36%. In operation this should be reflected by a reduction in power consumption also of 36%. Clearly it is desirable that the thickness of the thermally insulating member 2 be reduced as much as possible commensurate with maintaining sufficient thermal insulation to obtain sufficient temperature differentials between the sensor bodies 3 and 4 for the required sensitivity of the detector. In the limiting case where the member 2 has negligible thickness, the surface area, and power, reduction rises to nearly 43%. Clearly, also, heat loss can be reduced further by reducing the thickness of the sensor bodies 3 and 4. The reduction in heat loss rises to 50% in the limiting case where the sensor bodies have negligible thickness.

Figure 3:
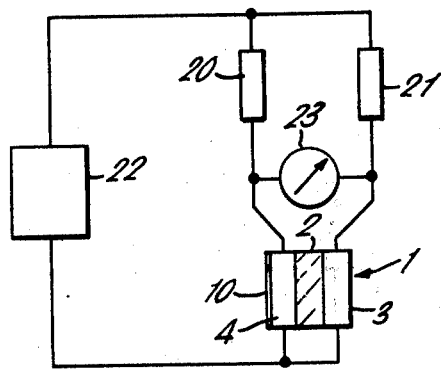
FIGS. 3 and 4 are respective examples of bridge circuits in which the sandwich detector may be connected.

Referring now to FIG. 3, the detector sandwich 1 is connected in a circuit which is effective to heat the sandwich to a desired temperature above ambient and is also responsive to temperature differentials between the sensors, resulting from exothermic or endothermic reactions at the catalytic coating 10. In FIG. 3, the two conductive paths of the detector sandwich 1 are connected in respective arms of a bridge circuit. Thus, the conductive path of the sensor body 4 with the catalytic coating 10 is connected in one arm of the bridge in series with a resistance 20, and the conductive path of the other sensor body 3 is connected in the other arm of the bridge in series with a resistance 21. A stabilised power supply 22 is connected across the bridge with the two arms of the bridge in parallel and a volt meter 23 is connected between the balance points of the bridge, i.e., between the connection point of resistor 20 and the path of sensor body 4 and the connection point of resistor 21 and the path of sensor body 3. When the two resistance thermometer sensor bodies 3 and 4 have substantially identical characteristics, as in the above described example, the two resistances 20 and 21 are of substantially equal values so that similar heating currents flow through the two conductive paths 7.

In a typical application, it is required to heat the sandwich detector to a temperature of 400° C., so that with a suitable composition of the catalytic coating 10 a combustion reaction can be detected of an inflammable gas such as methane. Using a sandwich detector of the dimensions in the above example, a total electrical power of approximately 1 watt is required to raise the temperature of the detector to 400° C. in typical room temperature ambient conditions. At the temperature of 400° C., the resistance of the conducting paths 7 rises to 25Ω. Thus considering that each resistance thermometer sensor body requires half of the total 1 watt the voltage across each conducting path 7 is approximately 3.5 volts. If the two resistance thermometer sensors 3 and 4 were employed without the sandwich construction embodying the present invention, the total power required to maintain them at 400° C., would be approximately 1.6 watts and the voltage across each conducting path would be nearly 4.5 volts. Thus, it can be seen that use of the present invention provides considerable improvement both in terms of power consumption and voltage requirements to heat the sensors.

In many applications of catalytic gas detectors, for example in coal mines, the detectors are run from batteries. Clearly any reduction in power dissipation is desirable to increase battery life or time between recharging accumulators. Furthermore, in potentially hazardous environments, such as in coal mines, it is a common requirement to design electrical equipment to be "intrinsically" safe, that is to operate with voltages and currents which are sufficiently small to minimise the risk of sparks or arcing resulting from circuit breaks. By reducing both the current consumption and voltage requirements for heating the detector, the requirements of intrinsic safety may more readily be met employing the present invention.

Figure 4:
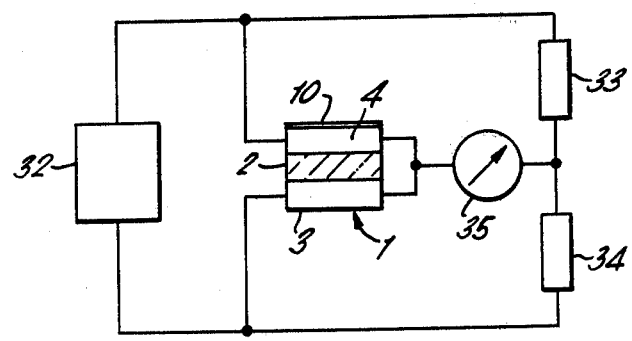

Considering now the circuit of FIG. 4 there is illustrated an alternative manner of connecting the sandwich detector 1 in a bridge circuit. In the circuit of FIG. 4, the two conducting paths 7 of the detector sandwich 1 are connected in series in the same arm of the bridge directly in series with a stabilised power supply 32. The other arm of the bridge comprises a pair of series connected resistors 33 and 34, connected in parallel with the detector sandwich 1. Once again a volt meter 35 is connected between the balance points of the bridge, i.e., between the point of connection of the conducting path 7 of the two sensor bodies 3 and 4 and the point of connection of the two resistors 33 and 34. Once again, if the electrical characteristics of the two resistance thermometer sensor bodies are closely matched, as in the above described example, then resistors 33 and 34 have substantially equal values, so that the bridge balances, with substantially no voltage reading at meter 35, when resistance thermometer sensor bodies 3 and 4 are at the same temperature. Assuming that identical currents through the conducting paths of the two resistance thermometer sensor bodies 3 and 4 maintain these bodies at the same temperature, the bridge will be balanced so long as no significant exothermic or endothermic reactions occur at the catalytic coating 10. However, if, for example, the detector sandwich 1 is exposed to a low concentration of an inflammable gas, a combustion reaction is catalysed at the coating 10, causing the temperature of sensor body 4 to rise relative to the temperature of body 3. The resulting increase in the resistance of the conducting path of sensor body 4 relative to that of sensor body 3 inbalances the bridge producing a voltage difference between the balance points. The voltage difference can be measured by volt meter 35 and the presence, and possibly the concentration of the inflammable gas can therefore be determined.

Clearly, using the same detector sandwich 1, the power dissipation in the sandwich in the circuit of FIG. 4 is the same as for the circuit of FIG. 3. However, the total power dissipation of the circuit of FIG. 4 can be less than that of FIG. 3. The value of resistors 33 and 34 can be very much greater than the resistance of the conducting paths 7, so that negligible power is dissipated in resistors 33 and 34. Thus the total power consumption of the circuit of FIG. 4 can be very little greater than the typically 1 watt dissipated in the detector sandwich. However, for the circuit of FIG. 3 resistors 20 and 21 must carry the same current as the respective conducting paths 7 with which they are connected in series. For maximum sensitivity of the circuit of FIG. 3 to temperature differentials between the sensor bodies 3 and 4, resistors 20 and 21 should be roughly equal to the resistance of the conducting paths 7 at the operating temperature, i.e. 25Ω in the above described example. Thus, an equal power is dissipated in resistors 20 and 21 as is dissipated in the detector sandwich 1. In practice, the sensitivity of the circuit can be sacrificed by reducing the value of resistors 20 and 21. However, significant power is still dissipated in resistors 20 and 21, as compared with resistors 33 and 34 of the circuit of FIG. 4.

Although power dissipation may be less for the circuit of FIG. 4, the power supply voltage may have to be greater. As shown above, the voltage across each conducting path 7 is typically 3.5 volts. Thus, the power supply 32 must have a voltage of 7 volts. Conversely, for the circuit of FIG. 3 the voltage of power supply 22 may be as low as say 4 volts, where resistors 20 and 21 have values lower than 25Ω. The reduction in supply voltages possible when using the circuit of FIG. 3 may be important from the consideration of intrinsic safety and this circuit may be more desirable in certain circumstances than the circuit of FIG. 4 in spite of the extra power dissipation.

We claim:

1. A catalytic gas detector formed as a sandwich comprising two resistance thermometer sensor bodies, the bodies being formed as substantially equally sized flat plates and being disposed in spaced substantially parallel planes, and a thermally insulating member sandwiched between the two plates such that the surface area of the sandwich is less than the combined surface area of the two sensor bodies, each said sensor body comprising a substrate of electrically insulating material and having thereon in thermal contact therewith a conducting path of material having a temperature dependent co-efficient of resistance, said thermally insulating member having a lower thermal conductivity than the material of said substrates and one of said sensor bodies having a catalytic coating on an exposed surface portion thereof.

2. A catalytic gas detector as claimed in claim 1 wherein, for each said sensor body, said conducting path comprises a conductive vitreous film deposited on a surface of said substrate facing said insulating layer.

3. A catalytic gas detector as claimed in claim 1 wherein said catalytic coating covers the entire exposed surface of one of said sensor bodies.

4. The catalytic gas detector as claimed in claim 1 including means to indicate a change in resistance of one of said conducting paths relative to the other conducting path.

5. A catalytic gas detector as claimed in claim 1, wherein said thermally insulating member comprises a substantially flat sheet of substantially the same size as said two flat sensor bodies.

6. A catalytic gas detector as claimed in claim 5, wherein said thermally insulating member comprises a refractory fiber mat.

7. A catalytic gas detector as claimed in claim 1 and in combination with an electrical circuit arranged for supplying current to said conducting paths of said two sensor bodies to heat said bodies to a predetermined temperature above ambient and responsive to relative changes in the temperatures of said two sensor bodies resulting from combustion or decomposition of a gas at the catalytic coating to provide an indication of the presence of said gas.

8. A catalytic gas detector and circuit combination as claimed in claim 7 wherein said electrical circuit is a bridge circuit and there is a meter connected between balance points of said bridge for indicating the presence of said gas.

9. A catalytic gas detector formed as a sandwich comprising two generally flat plate resistance thermometer sensor bodies oriented substantially parallel to each other and a thermally insulating member sandwiched between and contacting the two sensor bodies such that the surface area of the sandwich is less than the combined surface area of the two sensor bodies, each sensor body comprising a substrate of electrically insulating material and having mounted thereon in thermal contact therewith a conducting path of material having a temperature dependent co-efficient of resistance, said conducting paths being on the sides of the respective substrates adjacent the insulating layer, said thermally insulating member having a lower thermal conductivity than the material of said substrates, and one of said sensor bodies having a catalytic coating on an exposed surface portion thereon on a surface other than the surface on which the conducting path of the one sensor body is mounted.

* * * * *